United States Patent
Bischoff et al.

(10) Patent No.: US 11,076,917 B2
(45) Date of Patent: Aug. 3, 2021

(54) CONTROL DATA GENERATION FOR THE EYE SURGICAL TREATMENT OF DEFECTIVE VISION

(71) Applicant: Carl Zeiss Meditec AG, Jena (DE)

(72) Inventors: Mark Bischoff, Jena (DE); Gregor Stobrawa, Jena (DE); Michael Bergt, Weimar (DE)

(73) Assignee: Carl Zeiss Meditec AG, Jena (DE)

(*) Notice: Subject to any disclaimer, the term of this patent is extended or adjusted under 35 U.S.C. 154(b) by 103 days.

(21) Appl. No.: 16/233,902

(22) Filed: Dec. 27, 2018

(65) Prior Publication Data
US 2019/0201097 A1    Jul. 4, 2019

Related U.S. Application Data

(63) Continuation of application No. 13/810,169, filed as application No. PCT/EP2011/062067 on Jul. 14, 2011, now Pat. No. 10,166,073.

(30) Foreign Application Priority Data

Jul. 14, 2010 (DE) .................... 10 2010 031 348.3

(51) Int. Cl.
    *A61F 9/008*      (2006.01)
    *A61B 18/20*      (2006.01)
    *A61F 9/009*      (2006.01)

(52) U.S. Cl.
CPC .......... *A61B 18/20* (2013.01); *A61F 9/00829* (2013.01); *A61F 9/009* (2013.01);
(Continued)

(58) Field of Classification Search
CPC ...... A61B 18/20; A61F 9/00829; A61F 9/009; A61F 2009/00872; A61F 2009/00897
See application file for complete search history.

(56) References Cited

U.S. PATENT DOCUMENTS 4,685,180 A    8/1987   Kitaya
5,549,632 A    8/1996   Lai
(Continued)

FOREIGN PATENT DOCUMENTS

DE         695 00 997 T2    4/1998
DE    10 2006 053 118 A1    5/2008
(Continued)

OTHER PUBLICATIONS

Application and File History for U.S. Appl. No. 13/810,169, filed Mar. 29, 2013. Inventors: Mark Bischoff et al.

*Primary Examiner* — Nathan J Jenness
(74) *Attorney, Agent, or Firm* — Patterson Thuente Pedersen, P.A.

(57) ABSTRACT

A method for generating control data to control a laser device for correcting defective vision. A cut surface is specified which is curved, has a vertex and an edge, and is to be created in the eye. One or more paths, along which a focus of the laser radiation is to be adjusted, are defined for the control data and are selected such that they lie on or near the cut surface. To select the paths, a reference plane, preferably perpendicular, with respect to a direction of incidence of the laser radiation is determined, and different displacement positions are determined for said reference plane from the vertex to the edge of the cut surface. Multiple axes or semi-axes are determined for each displacement position. Intersections of the axes are connected into closed curves which are concentric or form a spiral.

20 Claims, 3 Drawing Sheets

(52) U.S. Cl.
CPC ............... *A61F 2009/00872* (2013.01); *A61F 2009/00897* (2013.01)

(56) References Cited

U.S. PATENT DOCUMENTS

| | | |
|---|---|---|
| 5,656,186 A | 8/1997 | Mourou et al. |
| 5,891,131 A | 4/1999 | Rajan et al. |
| 6,110,166 A | 8/2000 | Juhasz |
| 6,467,907 B1 | 10/2002 | Fujieda et al. |
| 6,635,051 B1 | 10/2003 | Hohla |
| 6,992,765 B2 | 1/2006 | Horvath et al. |
| 7,131,968 B2 | 11/2006 | Bendett et al. |
| 2004/0091537 A1 | 5/2004 | Miller |
| 2004/0092914 A1* | 5/2004 | Bille ............... A61F 9/00829 606/5 |
| 2004/0169820 A1 | 9/2004 | Dai et al. |
| 2004/0199150 A1 | 10/2004 | Lai |
| 2005/0107775 A1 | 5/2005 | Huang et al. |
| 2007/0179483 A1* | 8/2007 | Muhlhoff ............... A61F 9/008 606/10 |
| 2007/0293851 A1* | 12/2007 | Muhlhoff ............... A61F 9/008 606/11 |
| 2008/0077121 A1 | 3/2008 | Rathjen |
| 2008/0195086 A1 | 8/2008 | Schroeder et al. |
| 2008/0234707 A1 | 9/2008 | Muehlhoff et al. |
| 2008/0319428 A1 | 12/2008 | Wiechmann et al. |
| 2011/0034911 A1 | 2/2011 | Bischoff et al. |
| 2011/0208171 A1 | 8/2011 | Vegelsang et al. |

FOREIGN PATENT DOCUMENTS

| | | |
|---|---|---|
| DE | 10 2006 053 119 A1 | 5/2008 |
| DE | 10 2006 053 120 A1 | 5/2008 |
| DE | 10 2008 017 293 A1 | 10/2009 |
| DE | 10 2008 017 772 A1 | 10/2009 |
| EP | 1 153 584 A1 | 11/2001 |
| EP | 1 159 986 A2 | 12/2001 |
| EP | 1 897 520 A1 | 3/2008 |
| WO | WO 96/11655 A1 | 4/1996 |
| WO | WO 2004/032810 A2 | 4/2004 |
| WO | WO 2004/053568 A1 | 6/2004 |
| WO | WO 2005/011547 A1 | 2/2005 |
| WO | WO 2007/022993 A2 | 3/2007 |
| WO | WO 2008/055697 A1 | 5/2008 |

* cited by examiner

CONTROL DATA GENERATION FOR THE EYE SURGICAL TREATMENT OF DEFECTIVE VISION

CROSS-REFERENCE TO RELATED APPLICATIONS

The present application is a continuation of U.S. application Ser. No. 13/810,169 filed Mar. 29, 2013, entitled "Control Data Generation for the Eye-Surgical Treatment of Defective Vision" which is a National Phase entry of PCT Application No. PCT/EP2011/062067, filed Jul. 14, 2011, which claims priority from German Application Number 102010031348.3, filed Jul. 14, 2010, the disclosures of which are hereby incorporated by reference herein in their entirety.

FIELD OF THE INVENTION

The invention relates to a device and a method for generating control data, which are adapted to control a laser device emitting laser radiation for surgically correcting a defective vision of an eye, wherein a cutting surface is specified, which is curved, has a vertex and a border and is to be produced in the eye for correcting defective vision, for the control data one or more path curve(s) is/are defined, along which a focus of the laser radiation is to be shifted, the path curve(s) is/are selected such that it/they lie(s) in the cutting surface or within a tolerance zone around the cutting surface.

BACKGROUND

Spectacles are the traditional way of correcting defective vision in the human eye. However, refractive surgery which corrects defective vision by altering the cornea is now also increasingly being used. The aim of the operating methods is to selectively alter the cornea so as to influence refraction. Differing operating methods are known for this purpose. Currently the most widespread is the so-called laser-assisted in situ keratomileusis, also abbreviated to LASIK. Firstly, a lamella of the cornea is detached on one side from the cornea surface and folded to the side. This lamella can be detached by use of a mechanical microkeratome or also by use of a so-called laser keratome, such as is marketed e.g. by Intralase Corp., Irvine, USA. After the lamella has been detached and folded to the side, the use of an excimer laser, which removes the thus-exposed corneal tissue by ablation, is envisaged in the LASIK operation. After volume in the cornea has been vaporized in this manner the lamella of the cornea is folded back into its original place.

The use of a laser keratome to expose the lamella is advantageous as the danger of infection is thereby reduced and the cut quality increased. In particular the lamella can be produced with a very much more consistent thickness. The cut is also potentially smoother, which reduces subsequent sight problems due to this boundary surface which remains even after the operation.

To produce the cut, a series of optical perforations are made at predetermined points such that the cutting surface is formed as a result. With the laser keratome the cutting surface forms the lamella to be folded back before the use of laser ablation.

With the conventional LASIK method exposed corneal tissue is vaporized, which is also called "grinding" of the cornea by means of laser radiation. The volume removal which is necessary to correct defective vision is set for each surface element of the exposed cornea by the number of laser pulses and their energy. Therefore, in the LASIK method, a so-called shot file is provided for the ablation laser, which fixes, for different points on the cornea, how often, and with what energy, the laser beam is to be directed onto defined points on the cornea. The volume removal is heuristically determined, not least because it depends greatly on the ablation action of the laser beam, therefore on the wavelength, fluence etc. of the radiation used. The state of the cornea also plays a role; in particular the moisture content of the cornea is to be mentioned here. WO 96/11655 describes a device and a process for the LASIK method. In particular a formula is given which calculates the radius of curvature of the cornea to be achieved from the pre-operative radius of curvature of the cornea and the desired dioptre correction. A similar calculation is described in EP 1153584 A1—also for corneal ablation by means of LASIK.

A further laser-based eye-surgery method is not to vaporize the volume to be removed from the cornea, but to isolate it by a laser cut. The volume is thus no longer ablated, but isolated in the cornea by a three-dimensional cutting surface and thus made removable. Empirical values which have been developed for grinding the cornea by use of ablation laser radiation cannot be used for such methods. Instead, control data are required to operate the laser for isolating the volume to be removed from the cornea. One such eye-surgery method is described in U.S. Pat. Nos. 6,110,166 and 7,131,968. Different volume forms are shown in U.S. Pat. No. 6,110,166 and it is mentioned that the proper volume can be chosen by a person skilled in the art.

DE 102006053118 A1 describes the production of control data for the volume-isolating correction of defective vision.

It is known from DE 102006053120 A1 and DE 102006053119 A1 from Carl Zeiss Meditec AG to base the production of such control data on defective vision data which give the refractive power of spectacles suitable for correcting defective vision. It is also known from this published document, which thus describes a method according to the preamble and a device according to the preamble, to use data which also bring about a correction of an astigmatism or corrections of higher-order aberrations.

The precision with which the necessary cutting surfaces are produced is of great importance for volume-isolating correction of defective vision. Unlike with a laser keratome, the position of the cutting surfaces has a direct effect on the quality of the optical correction. With the conventional LASIK method, on the other hand, the precision with which the laser ablation is carried out is the only important factor determining the quality of the optical correction. This can already be seen from the fact that the cornea lamella is or has been produced in a large number of operations with a relatively crudely operating mechanical knife.

As the exact positioning of the eye is important for the precision production of the cutting surfaces, the state of the art, for example WO 2005/011547 A1, proposes that a contact lens, against which the cornea is pressed, can be used in laser-surgery devices. This contact lens serves to fix the eye.

However, the precise position of the eye is not the only important factor for the precision of the cutting surfaces; the shape of the cornea must also be known. As this varies from patient to patient within specific ranges, the contact lens also serves to give the cornea front surface a fixed, defined shape. When pressing the front of the cornea against the contact lens, there is consequently a deformation of the cornea which varies in size depending on the deviation of the curvature of the contact lens from the natural curvature of the cornea of the respective patient.

If the position of the cutting surfaces is important for the optical correction, i.e. if not just a lamella is isolated and the volume to be removed is removed by ablation, the deformation of the cornea is essential when determining the target coordinates for producing the cutting surfaces. Therefore it is known in the state of the art to take into account the deformation by subjecting the previously determined target points to a coordinate transformation. In the named WO publication, this transformation is called a "contact pressure transformation" and there are transformation equations for a combination of spherical contact lens and spherical cornea front surface. DE 102008017293 A1 from Carl Zeiss Meditec AG adds to these transformation equations with the result that coordinate transformation can also be carried out on different types of contact lens and cornea curvatures.

The invention thus relates to the concept of carrying out a correction of the optical imaging errors of the human eye by separating, by means of laser radiation within the cornea, a volume of tissue which is then removed from the cornea. A selective change of the refractive power of the cornea is thereby achieved. This change is localized, i.e. in the area of the cornea from which the tissue volume is removed. The pupil of the eye is usually taken as a basis.

The removal of the separated volume changes the geometry, i.e. the curvature of the cornea surface. In order that a desired correction of defective vision is achieved, the separated volume for removal must therefore have special properties with regard to its shape.

As already explained, for the eye-surgical correction of defective vision the curvature which the front surface of the cornea has after correction is decisive for the corrective effect. This surface shape therefore needs to be taken into consideration during the correction of defective vision isolating the volume. In the past, as already mentioned, the main focus was on a spherical or cylindrical correction. As the corresponding change in the front surface must take place on the non-deformed eye, it was particularly advantageous that these correction surfaces could be described analytically. In this case the transformation to be brought about by pressing on the contact lens could also be described analytically.

The advantage of analytical describability is particularly evident when the corresponding target points for the laser radiation are fixed and a path curve is defined, which connects the target points and along which the focus of a treatment lens radiation has to be shifted.

SUMMARY OF THE INVENTION

Until now it has therefore been relatively simple to determine the path curves so that rapid processing of the individual target points could be achieved. In the state of the art it is known to guide the laser beam along contour lines of the cutting surface or along a spiral which is based on contour lines of the cutting surface. The necessary breaking down of the cutting surface into contour lines or a contour lines spiral can be accomplished comparatively simply based on the simple analytical describability also of the transformed cutting surface.

However, if it is desired to make corrections by using cutting surface which can no longer be described analytically, or at least can no longer be described analytically in the transformed state, i.e. in the state of the eye in which the cutting surface is produced, it is extremely difficult to make a suitable choice of the target points or the path curve along which the target points are lined up.

The object of the invention is therefore to develop a method according to the type mentioned above or a device according to the type mentioned above, to define a corresponding path curve or corresponding path curves for any cutting surface, in particular one which cannot be represented analytically, which is to be produced in the eye in the status at the time of the operation (optionally deformed by a contact lens).

This object is achieved according to the invention with a method of the type named at the beginning, in which a reference plane which is at a predetermined angle, preferably perpendicular, to a direction of incidence of the laser radiation is defined and various shifting positions between the vertex and the border of the cutting surface are defined, for each shifting position several axes or semi-axes are defined, which lie in the reference plane, are not parallel to each other and, when viewed in a projection along the direction of incidence in the case of axes intersect within the edge of the cutting surface, or converge in the case of semi-axes within the edge of the cutting surface, for each shifting position of the reference plane intersection points of the axes or semi-axes with the cutting surface are determined, and the path curve(s) is/are fixed in that the intersection points are connected by means of an interpolation to form, when seen in a projection along the direction of incidence, concentric, closed curves or a spiral.

The object is further achieved with a device for generating control data, which are adapted to control a laser device emitting laser radiation for surgically correcting defective vision of an eye, wherein the device has: an interface for receiving interface data specifying a cutting surface which is curved, has a vertex and a border and is to be produced in the eye for correcting a defective vision, a calculation device which defines one or more path curve(s), along which a focus of the laser radiation is to be shifted, wherein the calculation device [selects] the path curve(s) according to the above method.

By concentric, closed curves are meant several curves each of which are closed, which do not intersect each other and can be drawn together at a common point. The path curve(s) thus lie(s) in the cutting surface or within a tolerance zone around the cutting surface.

The invention provides a method for decomposing a cutting surface into contour lines or into a spiral based on contour lines, in which a parametric representation of the cutting surface, which representation can either be mathematically very complicated, or even analytically impossible, is not required. With the help of the axes which are not parallel to each other and intersect in a reference plane, or semi-axes converging there, the cutting surface is broken down into discrete sampling points (or also function values). These axes (or semi-axes) are now shifted perpendicularly to the reference plane, which is equivalent to shifting the reference plane. Each shift corresponds to one shifting position. If it is desired to produce a spiral, the discrete function values are for example separated by a constant distance defined by the shifting positions.

The invention can work with intersecting axes. Alternatively it is also possible to work with semi-axes which converge at one point. It should be pointed out that working with semi-axes also makes it possible to choose an asymmetrical axis arrangement or to work with an uneven number of semi-axes, for example with semi-axes running from the centre to the apexes of a pentagon or similar. Where only axes are referred to hereafter, this is not intended to exclude the use of semi-axes.

The path curves (in the case of concentric closed curves) or the spiral running along the contour lines are (is) then obtained by piecewise radial interpolation between sampling points. It is expedient that the interpolation is effected piecewise between each two adjacent sampling points, i.e. intersection points, wherein transitions between two consecutive interpolation pieces are smooth. By smooth transitions are meant, within the meaning of this description, continuously differentiable transitions.

According to the invention, unlike in WO2005011547, a cutting surface can be factorized, independently of its analytical representation, into contour lines or a spiral based on contour lines. This is advantageous, in particular from the point of view of scanning speed, because for each surface $F:R^2 \rightarrow R^3$ in space there exists in each case a cutting line $H:R \rightarrow R^2$ with a plane being perpendicular to the slowest scanning dimension, which cutting line then lies in the two-dimensional subspace of the remaining, more rapid scanning dimensions. If the position of the plane perpendicular to the slowest scanning dimension is varied, this results in various cutting lines which have to be scanned in the subspace of the more rapid scanning dimensions. These lines are then contour lines relating to the slowest scanning dimension, whereby the focus shifting speed requirements are significantly reduced. To a person skilled in the art it is clear that a movement along adjacent contour lines can in principle take place in a spiral-shaped path curve. The direction followed by the spiral is not important, clockwise or anticlockwise. To a person skilled in the art inward or outward movements are covered by the concept.

With known scanning devices, the shifting speed is at its lowest along the optical axis (known as the z-axis). Therefore, fragmenting into contour lines preferably takes place in this spatial dimension. More abstractly, a parametric representation of the cutting surface F is sought, which does not change the z-positioning of the points on the surface when the one parameter is varied.

The already-mentioned contact pressure transformation has a problematic property. If it is applied to a contour line, in general the transformed curve is no longer a contour line. The object is therefore to find a method for calculating cutting lines in the contact pressure transformed state (contact lens system), which are contour lines there. This is a complicated mathematical problem, the solution of which can generally give rise to significant computational outlay, as contour lines or a spiral based thereon must be found on a surface which, as a rule, can no longer be analytically represented.

This is very involved, especially with cutting surfaces which have more than a 2-fold angular symmetry (with respect to rotation about the optical axis), such as occur in particular in the case of correction of higher-order vision defects.

Cylinder coordinates are advantageous for producing the closed path curves or the spiral based on contour lines. It is therefore preferred that the interpolation is done in cylinder coordinates, wherein the axes or semi-axes are selected so that in each shifting position a cylinder axis of the cylinder coordinates lies close to or coincides with an intersection point of the axes or common point of the semi-axes. The cylinder axis is perpendicular to the reference plane. The method saves a great deal of computational effort, particularly if all axes intersect on the cylinder axis. A symmetry of the cutting surface can be advantageously utilized if, furthermore, the cylinder axis runs from the vertex to the centre of the border of the cutting surface. With respect to the use on the laser device, it is moreover preferable if the cylinder axis coincides with the z-axis of the scanning device.

The number and angular positions $\varphi_k$ of the characteristic axes required to obtain the intersection points is in principle independent of the form of the cutting surface F to be decomposed. If one defines the number, and distributes the angular positions $\varphi_k$ for example evenly, the complexity of the surface thus approximated is also limited (sampling theorem). A large enough number of axes must thus be selected to achieve a good enough approximation between the path curve(s) $H(\varphi)$ determined in this way and the cutting surface F to be approximated. A large enough number of axes can for example be selected, so that the distance from the path curve(s) H to the cutting surface F is less than 10 µm, in particular less than 1 µm, in particular less than 0.1 µm.

However, the computational outlay for calculating the path curves rises increasingly with the number of the axes, and the complexity of the surface to be broken down is not always so great that a fixed predetermined number of axes is required. The number of the axes is therefore advantageously minimized and the number and position are selected so that they are suited to the complexity of the actual cutting surface. This leads to just as good an adaptation as the use of further axes.

The number of axes required for a specific cutting surface F is expediently determined from an angular symmetry of the surface. It is therefore preferred to determine a symmetry number describing the angular symmetry of the cutting surface and to select the number of the axes equal to the symmetry number. It is advantageous that the symmetry number is equal to the number of the axes of symmetry, which can be indicated for the cutting surface. For example, in the case of an elliptical cutting surface two axes of symmetry form, with the result that two axes can be used to determine the path curves.

With respect to the symmetry number it is preferred that, in order to determine the symmetry number, firstly a contour function $z(r, \varphi)$ of the cutting surface is determined on a circle with radius R and this contour function is then synthesized by a function series, wherein the symmetry number in the case of axes is fixed as the maximum order of the function series and, in the case of semi-axes, as double the maximum order which order is necessary to push a deviation between synthesized function and contour function below a preselected threshold value.

Thus, initially, a radial contour function $z(r, \varphi)$, periodic in $\varphi$, of the cutting surface F is determined on a circle with the radius R. Then a significance threshold is defined and the contour function synthesized by a Zernike or Fourier series up to the order at which the error of the contour function series is smaller than the significance threshold. The significance threshold is preferably less than 10 µm, in particular less than 1 µm, in particular less than 0.1 µm. The number of necessary axes is then equal to the maximum necessary order of the series. The angular positions of the axes can then be evenly distributed.

This analysis is preferably carried out for all radii $R <= R_{max}$, wherein $R_{max}$ is the maximum subsequent expansion of the cutting line e.g. of the rim of the cutting surface. The resultant maximum number of axes is used.

A further possibility for determining the number and position of characteristic axes is the number and position of the local extremes of the periodic radial contour function.

The axes (or semi-axes) are then always placed on the angular positions of all minimum and maximum values.

It is thus also possible to determine from the contour function the angular positions of local extremes of this contour function, and to place the axes on the angular positions of the local extremes. A uniform angular distribution is then not absolutely necessary. The procedure described above can equally be used for the production of closed concentric path curves, which at least approximate contour lines of the cutting surface, and for the production of a spiral which is based on such contour lines or path curves. The difference lies substantially in whether or not successively interpolated intersection points lie in the same shifting position of the reference plane, e.g. in the same z-plane. If the successively connected intersection points lie in the same plane, a path curve is obtained. If intersection points, which are arranged in different shifting positions (or z-positions) are connected, a spiral is obtained. In both procedures, however, intersection points obtained from adjacent-angle axes are always connected.

A precise indication of the angle of the axes is particularly simple, if all axes intersect at one intersection point or all semi-axes terminate in the same point. Such a selection of the axes is therefore preferred. The method according to the invention is not however restricted thereto, rather, there can also be several intersection points. The reference point for the angle indication or the point where the cylinder axis pierces the reference plane is then advantageously placed (or the axes are placed in relation to the cylinder axis) so that this reference point lies close to a common point of the axes (semi-axes). Referencing the location information then to the named reference point generally leads to a tolerable error, even so the location information should actually be related to the respective common point. Therefore, as a result, not all axes have to intersect at one point, even if this is to be preferred in view of reduced computational outlay.

It is understood that the features mentioned above and those yet to be explained below can be used, not only in the stated combinations, but also in other combinations or alone, without departing from the scope of the present invention.

The method according to the invention for generating the control data can be carried out without human involvement. In particular it can be carried out by a computer which carries out the method according to the invention under the control of a program according to the invention and determines the control data for the laser device from corresponding presets. In particular when determining the control data there is no need for the participation of a doctor as there is no therapeutic procedure involved in determining the control data. This takes place only when the previously determined control data are employed.

Where a method or individual steps of a method for determining control data for the correction of defective vision are described in this description, the method or individual steps of the method can be carried out using the correspondingly designed device. This applies analogously to the explanation of the mode of operation of a device which carries out the method steps. To this extent device and method features of this description are equivalent. In particular it is possible to realize the method with a computer on which a corresponding program according to the invention is executed.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

Figure 1:
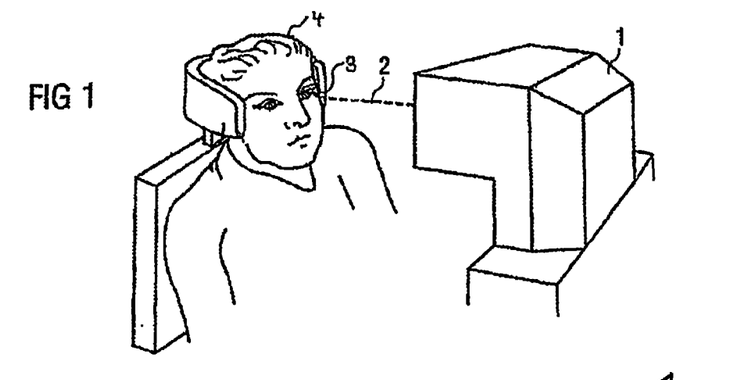
FIG. 1 is a schematic representation of a treatment device or apparatus for correcting defective vision.

FIG. 1 shows a treatment apparatus 1 for an eye-surgery method which is similar to that described in EP 1159986 A1 or in U.S. Pat. No. 5,549,632. By application of a treatment laser radiation 2 the treatment apparatus 1 brings about a correction of a defective vision on an eye 3 of a patient 4. Defective vision can include hyperopia, myopia, presbyopia, astigmatism, mixed astigmatism (astigmatism in which there is hyperopia in one direction and myopia in a direction lying at right angles thereto), aspherical errors and higher-order aberrations. In the embodiment described, the treatment laser radiation 2 is applied as a pulsed laser beam focused into the eye 3. The pulse duration is e.g. in the femtosecond range, and the laser radiation 2 acts by means of non-linear optical effects in the cornea. The laser beam has e.g. 50 to 800 fs short laser pulses (preferably 100-400 fs) with a pulse repetition frequency of between 10 and 500 kHz. In the embodiment described, the components of the apparatus 1 are controlled by an integrated control unit, which, however, can of course also be formed as a separate unit.

Before the treatment apparatus is employed, the defective vision of the eye 3 is measured by one or more measuring devices.

Figure 2:
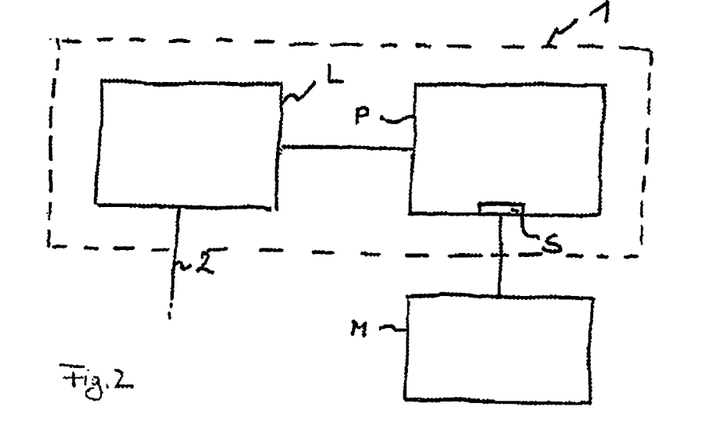
FIG. 2 is a schematic representation of the structure of the treatment apparatus of FIG. 1.

FIG. 2 shows the treatment apparatus 1 schematically. In this variant it has at least two devices or modules. A laser device L emits the laser beam 2 onto the eye 3. The operation of the laser device L in this case is fully automatic, i.e. in response to a corresponding start signal the laser device L starts to deflect the laser beam 2 and produces cutting surfaces which are constructed in a manner yet to be described and isolate a volume in the cornea. The laser device L receives the control data necessary for operation beforehand from a planning device P as a control data set, via control lines that are not identified in more detail. Data are transmitted prior to operation of the laser device L. Naturally, communication can also be wireless. As an alternative to direct communication, it is also possible to arrange the planning unit P physically separated from the laser unit L, and to provide a corresponding data transmission channel.

Preferably, the control data set is transmitted to the treatment apparatus 1 and, more preferably, operation of the laser device L is blocked until there is a valid control data set at the laser device L. A valid control data set can be a control data set which, in principle, is suitable for use with the laser device L of the treatment device 1. Additionally, however, the validity can be linked to the passing of further tests, for example whether details, additionally stored in the control data set, concerning the treatment apparatus 1, e.g. an appliance serial number, or concerning the patient, e.g. a patient identification number, correspond to other details that for example have been read out or input separately at the treatment device as soon as the patient is in the correct position for the operation of the laser device L.

From measurement data and defective-vision data which have been determined for the eye to be treated the planning unit P produces the control data set that is made available to the laser unit L for carrying out the operation. The data are supplied to the planning unit P via an interface S and, in the embodiment represented, come from a measuring device M which has previously taken measurements of the eye of the patient 4. Naturally, the measuring device M can transfer the corresponding measurement and defective-vision data to the planning device P in any desired manner.

Transmission can be by means of memory chips (e.g. by USB or memory stick), magnetic storage (e.g. disks), by radio (e.g. WLAN, UMTS, Bluetooth) or wired connection (e.g. USB, Firewire, RS232, CAN-Bus, Ethernet etc.). The same naturally applies with regard to the data transmission between planning device P and laser device L.

A direct radio or wired connection of measuring device M to treatment device 1 with regard to data transmission which can be used in a variant has the advantage that the use of incorrect measurement and defective-vision data is excluded with the greatest possible certainty. This applies in particular if the patient is transferred from measuring device M or measuring devices to the laser device L by means of a storage device (not represented in the Figure) which interacts with measuring device M or laser device L such that the respective devices recognize whether the patient 4 is in the respective position for measurement or introduction of the laser radiation 2. By bringing the patient 4 from measuring device M to laser device L the transmission of measurement and defective-vision data to the treatment device 1 can also take place simultaneously.

In an example embodiment it is ensured by suitable means that the planning device P always produces the control data set belonging to the patient 4 and an erroneous use of an incorrect control data set for a patient 4 is as good as excluded.

Figure 3:
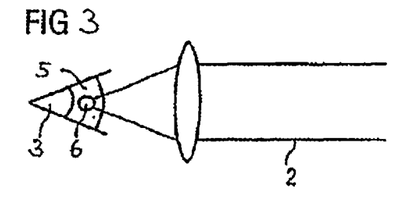
FIG. 3 is a presentation showing the principle of introducing pulsed laser radiation into the eye when correcting defective vision with the treatment apparatus of FIG. 1.

The mode of operation of the laser beam 2 is indicated schematically in FIG. 3. The treatment laser beam 2 is focused into the cornea 5 of the eye 6 by use of a lens that is not described in more detail. As a result there forms in the cornea 5 a focus 6 that covers a spot and in which the energy density of the laser radiation is so high that, in combination with the pulse length, a non-linear effect in the eye results. For example, each pulse of the pulsed laser radiation 2 can produce at the respective spot an optical break-through in the cornea 5 which, in turn, initiates a plasma bubble, indicated schematically in FIG. 3. As a result, tissue in the cornea 5 is separated [by application] of this laser pulse. When a plasma bubble forms, the tissue layer separation covers a larger region than the spot covered by the focus 6 of the laser radiation 2, although the conditions for producing the break-through are achieved only in the focus 6. In order for an optical break-through to be produced by every laser pulse, the energy density, i.e. the fluence, of the laser radiation must be above a certain threshold value which is dependent on pulse length. This relationship is known to a person skilled in the art from, for example, DE 69500997 T2.

Alternatively, a tissue-cutting effect can also be produced by the pulsed laser radiation by emitting several laser radiation pulses in a region, wherein the spots of several laser radiation pulses overlap. Several laser radiation pulses then interact to achieve a tissue-cutting effect.

The type of tissue cutting which the treatment apparatus 1 uses is, however, not further relevant for the description below, although pulsed treatment laser radiation 2 is described in this description. For example a treatment apparatus 1 such as is described in WO 2004/032810 A2 can be used. A large number of laser-pulse foci forms a cutting surface in the tissue, the shape of which depends on the pattern with which the laser-pulse foci 6 are/become arranged in the tissue. The pattern specifies target points for the focus position at which one or more laser pulse(s) is (are) emitted and defines the shape and position of the cutting surface.

In order now to carry out a correction of defective vision, material is removed from a region within the cornea 5 by application of the pulsed laser radiation by cutting tissue layers to isolate the material and then make it possible for material to be removed. The removal of material brings about a change in the volume of the cornea which results in a change in the optical imaging power of the cornea 5, which change is calculated with such precision that the previously determined defective vision thus is/becomes corrected as much as possible. To isolate the volume to be removed, the focus of the laser radiation 2 is directed towards target points in the cornea 5, generally in an area which is located beneath the epithelium and the Bowman's membrane and above the Decemet's membrane and the endothelium. For this purpose the treatment apparatus 1 has a mechanism for shifting the position of the focus of the laser radiation 2 in the cornea 5. This is shown schematically in FIG. 3.

As already mentioned, the laser radiation 2 is bundled in a focus 6 in the cornea 5, and the position of the focus 6 in the cornea is shifted such that, to produce cutting surfaces, energy from laser radiation pulses is introduced into the tissue of the cornea 3 focused at various points. The laser radiation 2 is provided by a laser as pulsed radiation. An xy scanner which, in a variant, is realized by two substantially orthogonally deflecting galvanometric mirrors deflects the laser beam from the laser in two dimensions such that there exists a deflected laser beam after the xy scanner. The xy scanner thus effects a shifting of the position of the focus 6 substantially perpendicular to the main direction of incidence of the laser radiation 2 into the cornea 5. To shift the depth position a z scanner is provided in addition to the xy scanner. The z scanner ensures that the z position of the focus 6 position, i.e. its position on the optical incidence axis, can be changed. The z scanner can be arranged before or after the xy scanner. The coordinates designated x, y, z in the following relate to the deflection of the position of the focus 6.

The allocation of the individual coordinates to the spatial directions is not essential for the operating principle of the treatment apparatus 1; but to simplify the description, in the following the coordinate along the optical axis of incidence of the laser radiation 2 is always designated z, and x and y designate two coordinates orthogonal to one another in a plane perpendicular to the direction of incidence of the laser beam. It is naturally known to a person skilled in the art that the position of the focus 6 in the cornea 5 can also be described three-dimensionally by other coordinate systems, in particular that the coordinate system need not be a rectangular coordinate system. Thus it is not essential for an xy scanner to deflect around axes that are at right angles to one another; rather, any scanner capable of shifting the focus 7 in a plane in which the incidence axis of the optical radiation does not lie can be used. Oblique-angled coordinate systems are thus also possible.

Further, non-Cartesian coordinate systems can also be used to describe, or control, the position of the focus 6, as will also be explained further below. Examples of such coordinate systems are in particular cylindrical coordinates.

To control the position of the focus 6, the xy scanner as well as the z scanner, which together realize some example of a three-dimensional focus-shifting device, are controlled by a control apparatus provided in the treatment apparatus (or separately). The same applies to the laser. The control device provides for an appropriately synchronous operation of the laser and of the three-dimensional focus-shifting device, realized exemplarily by the xy scanner and the z scanner, such that the position of the focus 6 in the cornea 5 is shifted in such a way that, ultimately, a defined volume of material is isolated, wherein the subsequent removal of this volume results in a desired correction of a defective vision.

The control apparatus operates according to predetermined control data which define the target points for shifting the focus. The control data are generally combined in a control data set. In one embodiment, this set predetermines the coordinates of the target points as a pattern, wherein the sequence of the target points in the control data set fixes the serial arrangement of the focus positions alongside one another and thus, ultimately, a path curve (also referred to here for short as a path). In one embodiment, the control data set contains the target points as actual control values for the focus position shifting mechanism, e.g. for the xy scanner and the z scanner. For the purpose of preparing the eye-surgery method, i.e. before the actual operating method can be performed, the target points, and also their sequence, are determined as a path curve. There must be pre-planning of the surgical procedure to the effect that the control data for the treatment apparatus 1 are determined, the application of which then achieves an optimal correction of defective vision for the patient 4.

Firstly, for this purpose the volume to be isolated in the cornea 5 and later removed must be determined. This is known in the state of the art.

Figure 4:
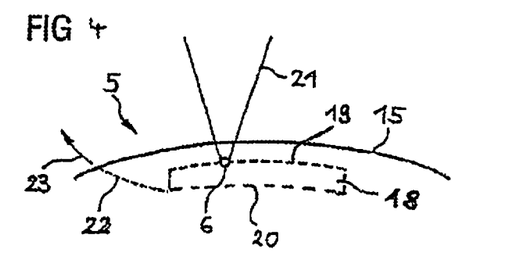
FIG. 4 is a schematic sectional representation through the cornea to illustrate volume removal.

The treatment apparatus 1 produces a curved cutting surface by application of the laser radiation 2, which is focussed into the eye. In the process the focus 6 is shifted along a path. This cutting surface, which can for example be the cutting surface 19 or 20 of FIG. 4, results when the focus 6 is shifted along a proper path curve. In order to reach a maximum speed of the cutting surface production, the path curve is selected so that the slowest shifting speed is also required along that shift axis which is the slowest. The slowest shift axis is usually the z-axis.

The cutting surface to be produced is therefore to be decomposed into one or more path curves which, relative to the z-axis, are based on contour lines of the cutting surface. Generating the path curve(s) is the decisive step when preparing the control data.

Figure 5:
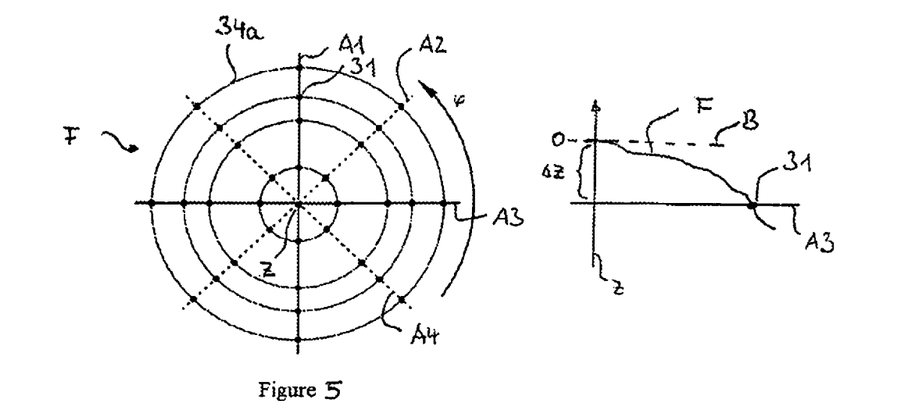
FIG. 5 is a schematic representation of a cutting surface with four axes for producing a path curve.

FIG. 5 exemplarily shows a top view of the cutting surface F in the form of a contour line diagram 30. It should be pointed out that this contour line diagram 30 serves only to illustrate the drawing. In fact the embodiment described here relates to cases in which a contour line diagram is not exactly available. For the cutting surface F axes are now defined, which do not lie parallel to each other and, in the described embodiment, run through the cylinder axis Z which, in the representation in FIG. 5, lies perpendicular to the drawing plane and is given the reference "Z". In the example in FIG. 5 four axes A1, A2, A3 and A4 are drawn.

These axes all lie in one reference plane and are now brought with this plane into different shifting positions along the z axis. In each shifting position intersection points 31 are determined, which the respective axis has with the cutting surface F. The right-hand part of FIG. 5 shows a corresponding sectional representation which is tilted at an angle of 90° to the top view of the left-hand part of FIG. 5. In this representation the axis A3 is shifted into a shifting position $\Delta z$ relative to the vertex (entered at z coordinate 0), in which the unshifted original reference plane B was located. An intersection point 31 is obtained.

The intersection points 31 obtained in the respective shifting positions for the axes are identified with respect to their cylinder coordinates, i.e. with respect to radius r and angle $\varphi$ and naturally with respect to the shifting position, i.e. the z coordinate. In the top view representation of the left-hand part of FIG. 5 a large number of intersection points 31 then result for the axes A1 to A4 in the different shifting positions, i.e. for different z coordinates.

These obtained intersection points 31 are now connected by an interpolation. If a set of closed path curves 34a is desired, the intersection points 31 which resulted in the same shifting position, i.e. with the same z coordinate, are connected. When doing so, intersection points 31 of adjacent sectors are connected by an interpolation p. The interpolation is done by varying the radius r from the angular position of the first intersection point 31 to the value which the radius r has at the angular position of the second intersection point 31. The interpolation is carried out piecewise and designed so that the individual pieces join together smoothly, i.e. continuously differentiably. This can for example be achieved in that a boundary condition of the interpolation requires to form at each intersection point the slope as a tangent to the respective radius.

If, instead of a set of closed path curves 34a, it is desired to obtain a spiral 34b which is based on contour lines, adjacent-angle intersection points 31 are also connected, wherein however at least within a 360° rotation, the shifting position is changed once, i.e. an intersection point 31 which has been determined with one z coordinate is connected to an intersection point 31 which lies in the next shifting position, i.e. has the next z coordinate.

Figure 6:
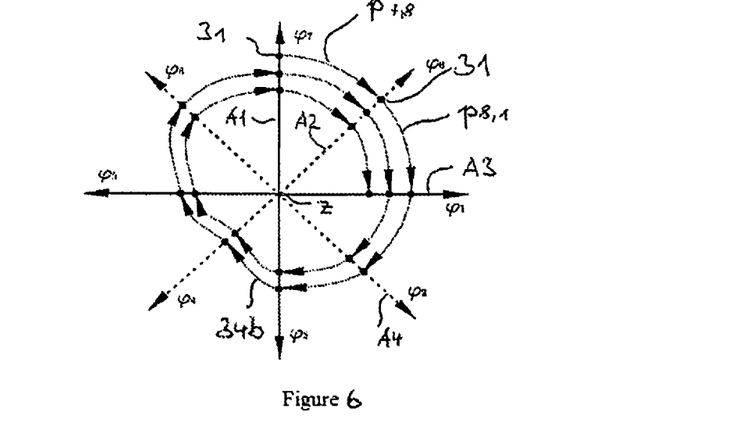
FIG. 6 is the associated path curve produced in the form of a spiral based on contour lines.

This procedure is illustrated exemplarily in FIG. 6. Here too, the four axes A1, A2, A3 and A4 are drawn in again, as are the intersection points 31 resulting for the various shifting positions wherein, due to the projection, this cannot be seen in FIG. 6. Angle values are allocated to each axis A1 to A4. Axis A1 has the angle values $\varphi_7$ and $\varphi_3$, axis A2 the angle values $\varphi_8$ and $\varphi_4$, axis A3 the angle values $\varphi_1$ and $\varphi_8$ and axis A4 the angle values $\varphi_2$ and $\varphi_6$. The two angle values of each axis differ by an angle of 180°. Alternatively it would also be possible to work with semi-axes. Each axis would then have its own angle value, and the number of axes would be doubled.

The piecewise interpolation is done in the example in FIG. 6 by application of functions which run from the angle of one axis to the angle of the next, for example from the angle $\varphi_7$ to the angle $\varphi_8$. Through this interpolation by application of an interpolation function, in this case $\varphi_{7,8}$, a piece of the path curve is obtained which leads from intersection point 31 of axis A1 to intersection point 31 of axis A2. In the simplest case, the interpolation piece $p_{7,8}$ produces a uniform adaptation of the radius, from the radius value which intersection point 31 of axis A1 has to the radius value which at intersection point 31 of axis A2 has. Similar interpolation pieces p follow such as for example interpolation piece $p_{8,1}$.

In the embodiment described here these interpolation pieces all still lie at the same z-coordinate, i.e. in the same shifting position of the axes. In the example shown, a change to the next shifting position first occurs between angles $\varphi_3$ and $\varphi_4$. This change is repeated at the next rotation, with the result that overall a spiral 34b is obtained, which follows contour lines between angles $\varphi_4$ and $\varphi_3$, i.e. remains at the same z coordinate, and passes over into the next shifting position, i.e. the next z coordinate or plane between angles $\varphi_3$ and $\varphi_4$.

Of course it is alternatively also possible to distribute the transition over a wider angle range, in particular to carry out it out uniformly over 360°. The intersection points 31 of adjacent-angle axes, for example of axes A1 and A2, then lie at different shifting positions. The procedure for piecewise interpolation by means of the interpolation function p is not, however, changed by this, as this interpolation function merely generates, over the angle between two consecutive angle values, a transition from the radius at the first angle value to the radius at the second angle value. During the piecewise interpolation the z coordinate is to be taken into consideration only in that, the z coordinate of the path function is correspondingly modified by the distance between the shifting positions, which corresponds to a z feed, dependent on angle $\varphi$. However, this is not taken into account in determining the radial transition. In other words, the interpolation function can be separated into a radial portion depending (only) on the angle and a z portion also depending (only) on the angle. This separation allows the interpolation function to be produced with little computation.

Figure 8:
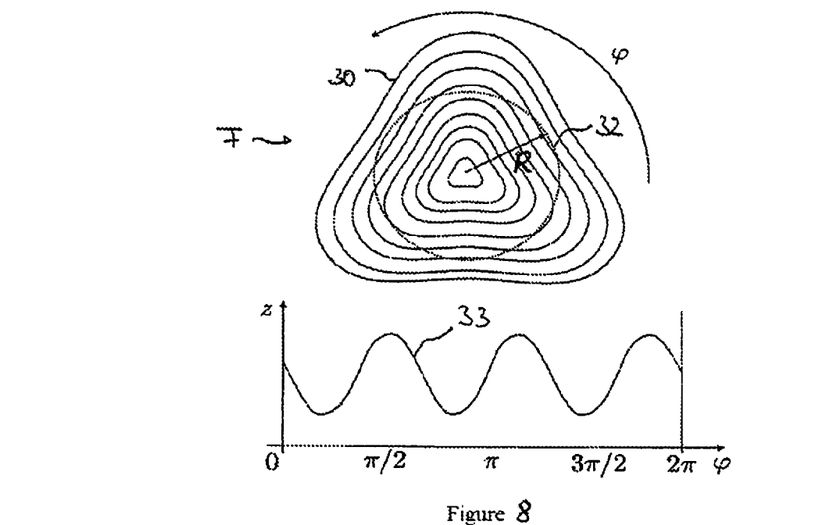
FIG. 8 is an illustration of the development of the function series of the surface in FIG. 7 in a contour function.
Figure 9:
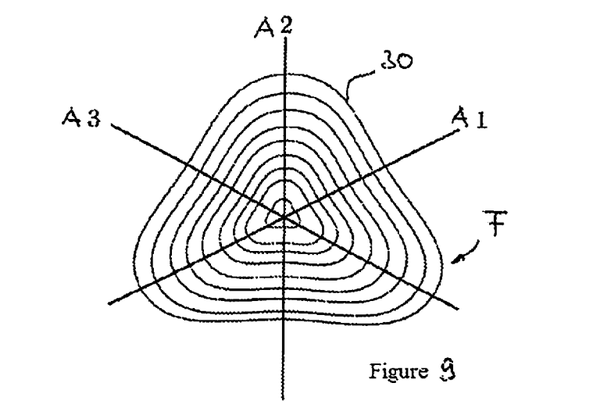
FIG. 9 is the cutting surface of FIG. 7 with the determined axes.

The position of the axes is decisive for determining the intersection points 31. As already mentioned in the general part of the description, it is advantageous to use the angular symmetry of the surface F here. This is explained exemplarily with reference to a cutting surface F having three-fold symmetry, which FIG. 7 shows again in form of contour line diagram 30. To define the position of the axes a radial contour function z (r, $\varphi$), periodic in $\varphi$, of the cutting surface F is now determined on a circle with radius R. This circle 32 is included exemplarily in FIG. 8. FIG. 8 shows the contour function 33 directly below. In the exemplary case, it is of course immediately recognized that the highest periodicity per rotation (2$\pi$) is three. Three axes A1 to A3 (or six semi-axes) are therefore sufficient, as shown by FIG. 9. For a more complex contour function it is advantageous to synthesize this function by a function series, for example a Fourier series or a Zernike polynomial series. If the contour function 33 were expanded by such a function series, it would be seen that, in the case of an expansion beyond the third order, no improved adaptation to the radial contour function is achieved.

In principle it is possible to achieve a better adaptation with a higher number of axes for many cutting surfaces F. On the other hand, there is the computational outlay which increases with the number of axes, as the number of intersection points 31 and the number of piecewise interpolations increase correspondingly. It is therefore advantageous to check the error of the function series from the contour function by means of a threshold value (also referred to as a significance threshold). The development of the function series is then interrupted if the deviations between the contour function and the function series remain below the threshold value.

In an alternative approach it is also possible to determine the extremes of the projection of the cutting surface F along the z axis (another axis can of course also be used). The number of the extremes indicates the number of the required axes. Three axes (or six semi-axes) would thus equally be obtained in the example in FIG. 7 or 9.

Figure 7:
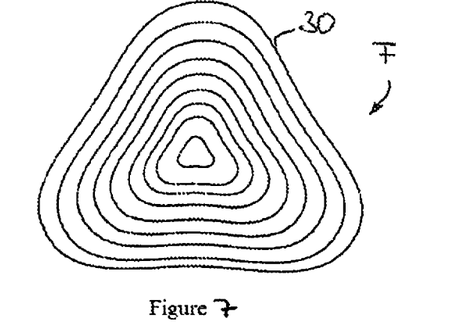
FIG. 7 is an exemplary cutting surface with three-fold symmetry.
Figure 10:
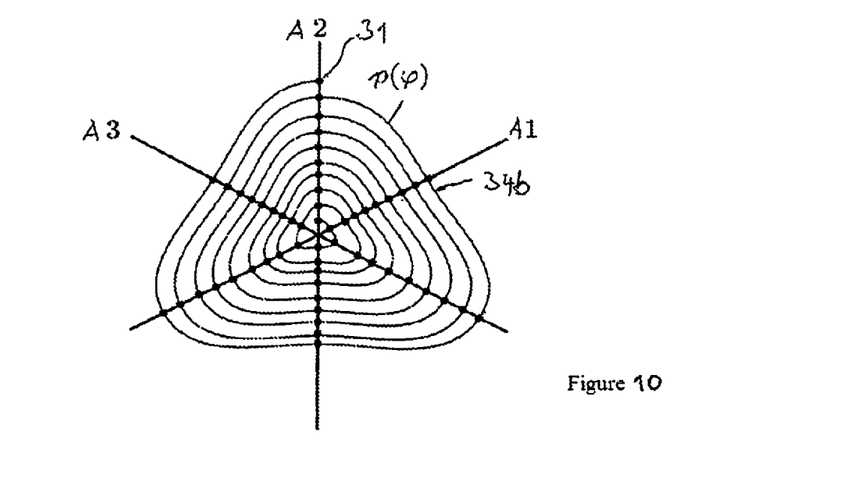
FIG. 10 is a representation of the cutting surface of FIG. 7 with determined intersection points and a spiral based on contour lines as path curve.

FIG. 10 shows the spiral-shaped path 34b, which is based on contour lines and was obtained by evaluating the intersection points 31 which the axes A1, A2 and A3 have in the cutting surface 11 in FIG. 7. Otherwise what was said with respect to FIG. 6 applies analogously to FIG. 10.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A method of surgically correcting optical imaging errors of the eye by separating layers of tissue in the eye to mitigate defective vision of an eye, the method comprising:
defining at least one three dimensional cutting surface in a cornea of the eye;
using a laser device emitting laser radiation to direct the laser radiation to a focus position located in a cornea of the eye at a depth position in the cornea by control of a z-scanner;
producing the at least one three dimensional cutting surface in the cornea thereby isolating a volume within the cornea;
producing the at least one three dimensional cutting surface by shifting the focus position along at least one path curve which lies in the cutting surface or within a tolerance zone around the cutting surface;
making the three dimensional cutting surface angularly symmetrical with respect to rotation around an optical axis of the eye;
adjusting the focus position by operation of the z-scanner according to a depth position based on a contour function when shifting the focus position along the at least one path curve in concentric curves or a spiral revolving the focus position around the optical axis of the eye when viewed in a projection along a direction of incidence of the laser radiation; and
making the depth position based on the contour function dependent on a rotational angle around the optical axis of the eye, to have a periodicity and to be substantially periodically varying in the rotational angle.

2. The method of claim 1, further comprising:
emitting the laser radiation as pulsed laser radiation;
directing the pulsed laser radiation into the cornea; and
producing the at least one cutting surface by generating a series of optical breakthroughs in the cornea and below a front surface of the cornea.

3. The method of claim 1, further comprising making the depth position, which is dependent on the rotational angle, comprise a sequence of maxima and minima with the occurrence of maxima and minima being periodically within the rotational angle according to the periodicity of the contour function.

4. The method of claim 1, further comprising describing the angular symmetry of the cutting surface by a symmetry number and selecting the periodicity of the contour function to correspond to the symmetry number.

5. The method of claim 1, further comprising adjusting the focus position according to the contour function when seen along a direction of incidence of the laser radiation.

6. The method of claim 5, further comprising making the contour function a spiral revolving the focus position around the optical axis of the eye.

7. The method of claim 1, further comprising generating control data, which are adapted to control the laser device to produce the at least one cutting surface.

8. The method of claim 1, further comprising:
specifying the at least one cutting surface in relation to a natural un-deformed state of the cornea, wherein the cutting surface is curved, has a vertex and a border;
deforming the cornea to a transformed state by pressing a contact lens onto the cornea; and
determining the at least one path curve in relation to the transformed state of the cornea such that the at least one path curve lies in the cutting surface or within the tolerance zone around the cutting surface in relation to a natural un-deformed state.

9. The method of claim 8, the step of determining the at least one path curve further comprising:
defining a reference plane which is at a predetermined angle to a direction of incidence of the laser radiation and defining various shifting positions between the vertex and the border of the cutting surface for the reference plane;
defining for each shifting position several axes or semi-axes, which lie in the reference plane, are not parallel to each other and which, when viewed in a projection along a direction of incidence, in the case of axes, intersect within the border of the cutting surface and in the case of semi-axes, have at least one common point within the border of the cutting surface;
determining for each shifting position of the reference plane, intersection points of the axes or semi-axes with the cutting surface; and
wherein the at least one path curve is fixed in that the intersection points are connected by application of an interpolation to form concentric, closed curves or a spiral, when viewed in a projection along the direction of incidence.

10. The method according to claim 9, further comprising defining the reference plane to be perpendicular to the direction of incidence of the laser radiation.

11. A device for generating control data, which are adapted to control a laser device emitting laser radiation for surgically correcting optical imaging errors of an eye, the device being operably coupled to the laser device emitting laser radiation and in control thereof comprising:
an interface for receiving correction data specifying the optical imaging errors; and
a calculation device configured to define at least one three dimensional cutting surface in a cornea of the eye;
the calculation device being configured to specify the three dimensional cutting surface adapted to isolate a volume within a cornea of the eye by application of laser radiation applied from the laser device for correcting the optical imaging errors by removal of the volume from the cornea;
the calculation device further being configured to make the three dimensional cutting surface angularly symmetrical with respect to rotation around an optical axis of the eye;
the calculation device being configured to define at least one path curve, along which a focus of the laser radiation is to be shifted, which path curve lies in the cutting surface or within a tolerance zone around the cutting surface; and
the calculation device being configured to specify a depth position controlled by operation of a z-scanner for the at least one path curve;
wherein the depth position is based on a contour function and controlled by operation of the z-scanner, has a periodicity and is dependent on a rotational angle around the optical axis of the eye and is substantially periodically varying in the rotational angle, and
wherein the calculation device is configured to generate the control data such that the control data control the laser device to move a position of the focus of the laser radiation along the at least one path curve in concentric curves or a spiral revolving the focus position around the optical axis of the eye when viewed in a projection along a direction of incidence of the laser radiation.

12. The device according to claim 11, wherein the calculation device is configured to generate the control data such that the depth position based on the contour function, which is dependent on the rotational angle, comprises a sequence of maxima and minima with the occurrence of maxima and minima occurring periodically within the rotational angle according to the periodicity of the contour function.

13. The method according to claim 1, further comprising adjusting the focus position according to closed curves being concentric to a center of symmetry of the angularly symmetrical three dimensional cutting surface.

14. The device according to claim 11, wherein the calculation device is further configured to describe the angular symmetry of the cutting surface by a symmetry number and to select the periodicity of the contour function to correspond to the symmetry number.

15. The device according to claim 11, wherein the calculation device is configured to generate the control data such that the at least one path curve comprises a contour function when seen along a direction of incidence of the laser radiation, wherein the one path curve comprises a spiral when viewed in the projection along the direction of incidence.

16. The device according to claim 11,
further comprising a contact lens that can be pressed onto the cornea;
wherein the cornea is deformed to a transform state by application of the contact lens;
wherein the calculation device is configured to generate the control data such that the control data are adapted to control the laser device wherein the calculation device is further configured to specify the at least one cutting surface in relation to a natural un-deformed state of the cornea, wherein the cutting surface is curved, has a vertex and a border, and further configured to determine the at least one path curve in relation to the transformed state of the cornea such that the at least one path curve lies in the cutting surface or within the tolerance zone around the cutting surface in relation to a natural un-deformed state.

17. The device according to claim 16, wherein the calculation device is further configured
to define a reference plane which is at a predetermined angle to a direction of incidence of the laser radiation and defining various shifting positions between the vertex and the border of the cutting surface for the reference plane;
to define, for each shifting position several axes or semi-axes, which lie in the reference plane, are not parallel to each other and which, when viewed in a projection along a direction of incidence, in the case of axes, intersect within the border of the cutting surface and in the case of semi-axes, have at least one common point within the border of the cutting surface;
to determine, for each shifting position of the reference plane, intersection points of the axes or semi-axes with the cutting surface; and
wherein the at least one path curve is fixed in that the intersection points are connected by application of an interpolation to form concentric, closed curves or a spiral, when viewed in a projection along the direction of incidence.

18. The device according to claim 11, wherein the calculation device is further configured to generate the control data such that the focus position is adjusted according to closed curves being concentric to a center of symmetry of the angularly symmetrical three dimensional cutting surface.

19. A non-transitory computer readable data storage medium that is not a carrier wave or signal, comprising instructions that cause a computer to generate control data, which are adapted to control a laser device emitting laser radiation for surgically correcting optical imaging errors of an eye, the instructions comprising:
specifying at least one three dimensional cutting surface adapted to isolate a volume within a cornea of the eye by application of laser radiation applied from the laser device for correcting the optical imaging errors by removal of the volume from the cornea;
making the three dimensional cutting surface angularly symmetrical with respect to rotation around an optical axis of the eye;
defining at least one path curve, along which a focus of the laser radiation is to be shifted, which path curve lies in the cutting surface or within a tolerance zone around the cutting surface;
specifying a depth position controlled by operation of a z-scanner for the at least one path curve, wherein the depth position based on a contour function is controlled by operation of the z-scanner and is dependent on a rotational angle around the optical axis of the eye and has a periodicity substantially periodically varying in the rotational angle; and
generating the control data such that the control data control the laser device to move a focus position of the focus of the laser radiation along the at least one path curve in concentric curves or a spiral revolving the focus position around the optical axis of the eye when viewed in a projection along a direction of incidence of the laser radiation.

20. The non-transitory computer readable data storage medium that is not a carrier wave or signal according to claim 19, wherein the instructions further comprise: adjusting the focus position according to closed curves being concentric to a center of symmetry of the angularly symmetrical three dimensional cutting surface.

* * * * *

UNITED STATES PATENT AND TRADEMARK OFFICE
CERTIFICATE OF CORRECTION

PATENT NO. : 11,076,917 B2  
APPLICATION NO. : 16/233902  
DATED : August 3, 2021  
INVENTOR(S) : Mark Bischoff et al.

Page 1 of 1

It is certified that error appears in the above-identified patent and that said Letters Patent is hereby corrected as shown below:

In the Claims

Column 17, Line 35, delete "device" and insert --device,--

Signed and Sealed this  
Twenty-second Day of February, 2022

Drew Hirshfeld  
*Performing the Functions and Duties of the*  
*Under Secretary of Commerce for Intellectual Property and*  
*Director of the United States Patent and Trademark Office*